United States Patent
Nakazono et al.

(10) Patent No.: US 10,153,066 B2
(45) Date of Patent: Dec. 11, 2018

(54) CONDUCTIVE PASTE AND MULTILAYER BOARD USING THE SAME

(71) Applicant: TATSUTA ELECTRIC WIRE & CABLE CO., LTD., Higashiosaka-shi, Osaka (JP)

(72) Inventors: Hajime Nakazono, Kizugawa (JP); Norihiro Yamaguchi, Kizugawa (JP)

(73) Assignee: Tatsuta Electric Wire & Cable Co., Ltd., Osaka (JP)

( * ) Notice: Subject to any disclaimer, the term of this patent is extended or adjusted under 35 U.S.C. 154(b) by 0 days.

(21) Appl. No.: 15/509,139

(22) PCT Filed: Feb. 17, 2016

(86) PCT No.: PCT/JP2016/000837
§ 371 (c)(1),
(2) Date: Mar. 6, 2017

(87) PCT Pub. No.: WO2016/136204
PCT Pub. Date: Sep. 1, 2016

(65) Prior Publication Data
US 2017/0358381 A1    Dec. 14, 2017

(30) Foreign Application Priority Data

Feb. 27, 2015    (JP) .................................. 2015-038748

(51) Int. Cl.
*H01B 1/22* (2006.01)
*C07C 39/04* (2006.01)
(Continued)

(52) U.S. Cl.
CPC ............... *H01B 1/22* (2013.01); *C07C 39/04* (2013.01); *C07C 39/14* (2013.01); *H05K 1/11* (2013.01); *H05K 3/46* (2013.01); *H05K 3/4667* (2013.01)

(58) Field of Classification Search
CPC ........... H01B 1/22; C07C 39/04; C07C 39/14; H05K 1/11; H05K 3/4667
(Continued)

(56) References Cited

U.S. PATENT DOCUMENTS

2006/0057340 A1* 3/2006 Umeda .................... H01B 1/22
                                                         428/209
2014/0346413 A1* 11/2014 Inoue .................... H01B 1/026
                                                          252/514

FOREIGN PATENT DOCUMENTS

JP    2003-027102 A    1/2003
JP    2006-012734 A    1/2006
(Continued)

*Primary Examiner* — Harold Y Pyon
*Assistant Examiner* — Danny N Kang
(74) *Attorney, Agent, or Firm* — Norris McLaughlin, P.A.

(57) ABSTRACT

A conductive paste having a viscosity suitable for filling a hole of a board, long pot life, and excellent conductivity and long-term reliability of a cured product, and a multilayer board using the same are provided.

A conductive paste comprising with respect to (A) 100 parts by mass of dimer acid-modified epoxy resin, (B) from 200 to 1900 parts by mass of high melting metal powder containing silver-coated copper alloy powder and having a melting point of 800° C. or higher, (C) from 400 to 2200 parts by mass of silver-coated copper alloy powder having a melting point of 800° C. or higher, (D) from 1.0 to 20.0 parts by mass of curing agent containing a hydroxy group-containing aromatic compound, and (E) from 5.0 to 100.0 parts by mass of a flux containing polycarboxylic acid, is used as the present invention.

14 Claims, 1 Drawing Sheet

(51) Int. Cl.
*H05K 1/11* (2006.01)
*H05K 3/46* (2006.01)
*C07C 39/14* (2006.01)

(58) Field of Classification Search
USPC .......................................................... 252/500
See application file for complete search history.

(56) References Cited

FOREIGN PATENT DOCUMENTS

| | | | |
|---|---|---|---|
| JP | 2008-108625 A | | 5/2008 |
| JP | 2008-108629 A | | 5/2008 |
| JP | 2009-252507 A | | 10/2009 |
| JP | 2011-029204 A | | 2/2011 |
| JP | 2011029204 A | * | 2/2011 |
| JP | 2011-148951 A | | 8/2011 |
| JP | 2014-005531 A | | 1/2014 |
| JP | 2015-032806 A | | 2/2015 |
| WO | 03/105160 A1 | | 12/2003 |

* cited by examiner

CONDUCTIVE PASTE AND MULTILAYER BOARD USING THE SAME

TECHNICAL FIELD

The present invention relates to a conductive paste, and, in more detail, relates to a conductive paste for uses such as filling a hole of a board, a conductive adhesive, electrode formation, component packaging, electromagnetic wave shielding, conductive bump formation and the like, and a multilayer board using the conductive paste.

BACKGROUND ART

A metal melting paste is known as one of conductive pastes to be used for filling a hole of a board and so on. The paste is obtained by mixing a conductive filler with a flux, a curing agent and a thermosetting resin, and the resin is cured and metal powders are fused and metallized by a means that the paste is heated under certain conditions (for example, Patent Document 1). In such a paste, metal powders themselves are integrated with each other as well as a metal powder is integrated with an end surface of a conductive layer in a via hole. Therefore, high conductivity is obtained in comparison with the case where metal powders are merely brought into contact with each other or the metal powder is merely brought into contact with an end surface of a conductive layer, and reliability of connection at the end surface of the conductive layer is also remarkably improved.

However, in the conventional metallized paste, a silver powder or a silver-coated copper powder has been used as the metal powder. Good conductivity is obtained by using these powders but a silver powder is expensive. Furthermore, there is a problem that long-term reliability is not sufficient because it is difficult to coat the copper powder entirely with silver.

On the other hand, the conductive paste is required to have high storage stability and long pot life.

In recent years, a silver-coated copper alloy powder obtained by coating the surface of a copper alloy with silver is put into practical use as a metal powder that is inexpensive and has improved storage stability in comparison with a silver powder (for example, Patent Document 2).

However, even though such a silver-coated copper alloy powder is used in the preparation of a conductive paste, it does neither prolong pot life of the paste nor improve conductivity of a cured product and its long-term reliability.

PRIOR ART DOCUMENTS

Patent Document

Patent Document 1: JP-A-2008-108629
Patent Document 2: JP-A-2014-005531

SUMMARY OF THE INVENTION

Problems that the Invention is to Solve

The present invention has been made in view of the above problems and it aims to provide a conductive paste which has viscosity suitable for filling a hole of a board and long pot life, and which can give a cured product having excellent conductivity and long-term reliability. The present invention further aims to provide a multilayer board having excellent long-term reliability by using the conductive paste.

Means for Solving the Problems

To solve the above-mentioned problems, a conductive paste of the present invention comprises 100 parts by mass of dimer acid-modified epoxy resin, (B) from 200 to 1900 parts by mass of low melting metal powder having a melting point of 240° C. or lower, (C) from 400 to 2200 parts by mass of high melting metal powder containing silver-coated copper alloy powder and having a melting point of 800° C. or higher, (D) from 1.0 to 20.0 parts by mass of at least one curing agent containing a hydroxy group-containing aromatic compound, and (E) from 5.0 to 100.0 parts by mass of a flux containing polycarboxylic acid.

In the conductive paste, the silver-coated copper alloy powder contained in the component (C) is preferably copper alloy powder which contains from 1 to 40 mass % of zinc and/or from 1 to 40 mass % of nickel and which is coated with a silver alloy layer having a silver content of from 7 to 50 mass %.

The low melting metal powder contained in the component (B) may be indium alone and/or, one element or an alloy of at least two elements selected from the group consisting of tin, lead, bismuth and indium.

The hydroxy group-containing aromatic curing agent (D) may be one kind or a combination of at least two kinds selected from the group consisting of a phenol type curing agent and a naphthol type curing agent.

A multilayer board of the present invention comprises a plurality of conductive layers and insulating layers interposed among those conductive layers, wherein holes penetrating through the insulating layers are filled with cured conductive paste, and the conductive layers contacting both surfaces of the insulating layer electrically conduct with each other through the cured conductive paste, wherein the cured conductive paste is the one according to the present invention. It is preferred that the low melting metal powder and high melting metal powder are fused to integrate with each other, and are alloyed in the cured conductive paste.

Advantageous Effects of the Invention

The conductive paste of the present invention has a viscosity suitable for filling a hole of a board and long pot life, and cure products of the paste has remarkably excellent conductivity and long-term reliability. Therefore, the conductive paste that is preferably used for hole filling of an electronic board and has high long-term reliability may be obtained.

The multilayer board in which the conductive paste of the present invention has been used for filling a hole has improved reliability of connection between an end surface of the conductive layer in the hole and metal particles in the conductive paste, and pattern with high precision can be formed on it.

MODE FOR CARRYING OUT THE INVENTION

Figure 1A:
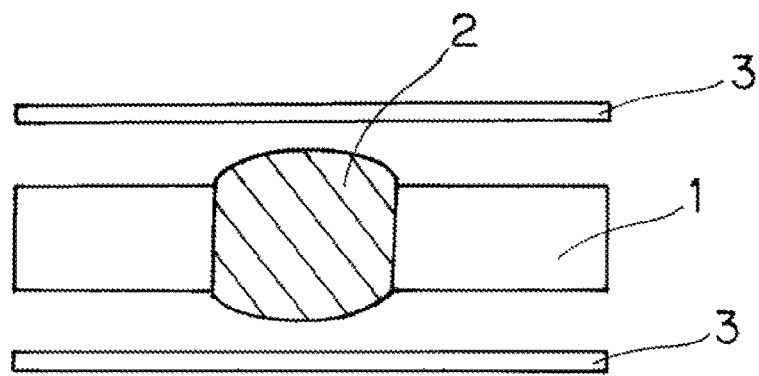
FIGS. 1(a), 1(b) and 1(c) are enlarged schematically cross-sectional views showing an example of the production of a board using the conductive paste of the present invention.

Embodiments of the conductive paste according to the present invention and the multilayer board using the same are described in detail below, but the invention is not construed as being limited to those. In the present description, a conductive paste after cured is also sometimes called "conductive paste" for convenience.

The conductive paste of the present invention contains dimer acid-modified epoxy resin (A). The dimer acid-modified epoxy resin employed in the present invention is an epoxy resin modified with dimer acid, that is, a resin in which at least one carboxyl group in a dimer acid structure has been reacted with a polyfunctional epoxy resin. The dimer acid employed herein is a dimer of unsaturated fatty acid, and the unsaturated fatty acid as a raw material is not particularly limited. For example, a plant-derived oil mainly including unsaturated fatty acid having 18 carbon atoms, such as oleic acid or linoleic acid, can be suitably employed. The structure of the dimer acid may be cyclic or non-cyclic. The type of the epoxy resin is not limited either. For example, the conventional dimer acid-modified epoxy resins obtained by modifying various epoxy resins such as bisphenol type, ether ester type, novolac epoxy type, ester type, aliphatic type, aromatic type and so on with dimer acid can be suitably employed. Examples of the commercially available products of the dimer acid-modified epoxy resin include "jER871" (trade name, hereinafter the same) and "jER872" manufactured by Mitsubishi Chemical Corporation, and "YD-171" and "YD-172" manufactured by Nippon Steel Chemical Co., Ltd.

Although the epoxy equivalent of the dimer acid-modified epoxy resin is not particularly limited, the number of grams of a resin containing an epoxy group of 1 gram equivalent measured by the method according to JIS K 7236 is in a range preferably from 100 to 800 g/eq., and more preferably from 300 to 600 g/eq. The molecular weight of the dimer acid-modified epoxy resin is not particularly limited, and can be suitably selected depending on the intended use. For example, the dimer acid-modified epoxy resin having a mass average molecular weight from 100 to 5000 can be preferably employed for a use of filling a hole.

As the dimer acid-modified epoxy resin, one kind or a combination of two or more kinds can be employed.

Other than the dimer acid-modified epoxy resin, one kind or a combination of two or more kinds of epoxy resins can be employed in the conductive paste of the present invention if necessary, for the purpose of improving printability and so on. The epoxy resin other than the dimer acid-modified epoxy resin can be any epoxy resin so long as it has at least one epoxy group in the molecule. Specific examples of the epoxy resin include bisphenol A type epoxy resin, brominated epoxy resin, bisphenol F type epoxy resin, novolac type epoxy resin, alicyclic epoxy resin, glycidyl amine type epoxy resin, glycidyl ether type epoxy resin and heterocyclic epoxy resin.

In the case that the epoxy resin other than the dimer acid-modified epoxy resin is employed, the content thereof is preferably 50 parts by mass or less with respect to 100 parts by mass of the dimer acid-modified epoxy resin.

Besides, an alkyd resin, a melamine resin, a xylene resin and the like can also be employed as a resin modifier.

The metal powder employed in the conductive paste of the present invention contains at least one kind of low melting metal powder (B) having a melting point of 240° C. or lower and at least one kind of high melting metal powder (C) having a melting point of 800° C. or higher containing a silver-coated copper alloy powder, and these powders cause metallization by being heated.

The metal powder employed in the present invention can be made of one single element of metal or of an alloy of at least two elements of metals. As the low melting metal powder, for example, powder of indium (melting point: 156° C.) itself, or powder have a melting point of 180° C. or lower made of one element or an alloy of at least two elements selected from the group consisting of tin (melting point: 231° C.), lead (melting point: 327° C.), bismuth (melting point: 271° C.) and indium can be used. It is preferred that tin is contained in the low melting metal powder. Examples of such include an alloy of tin (Sn) and bismuth (Bi), an alloy of tin (Sn), bismuth (Bi) and copper (Cu), and an alloy of tin (Sn), bismuth (Bi) and silver (Ag). Above all, an alloy of tin (Sn) and bismuth (Bi) is preferred, and it is particularly preferred that the alloy ratio of Sn and Bi (Sn:Bi) is in the range from 80:20 to 42:58. These low melting metal powders may be used as a combination of two or more kinds.

The high melting metal powder having a melting point of 800° C. or higher employed in the present invention preferably contains silver-coated copper alloy powder having a melting point of 800° C. or higher. The silver-coated copper alloy powder is preferably a copper alloy powder containing at least one element of nickel and zinc, which is coated with a silver-containing layer. More preferably, it may be copper alloy powder containing from 1 to 40 mass % of zinc and/or from 1 to 40 mass % of nickel, which is coated with a silver-containing layer (namely, a coating layer comprising silver or a silver compound). The coating amount of the silver-containing layer is preferably from 5 to 20 mass %, and more preferably from 5 to 10 mass %, in the amount of the silver-coated copper alloy powder.

As described above, when the copper alloy powder containing zinc and/or nickel and having the silver-containing layer is employed, the conductivity is equivalent to or better than those of copper powder and silver-coated copper powder, and pot life and long-term reliability thereof can be further improved. In particular, since zinc contributes to the improvement of conductivity and nickel contributes to the improvement of long-term reliability, it is preferred to adjust the proportion of both depending on intended use of the conductive paste. The content of each of zinc and nickel is preferably from 1 to 30 mass %, and more preferably from 1 to 15 mass %, depending on the intended purpose.

For example, in the case where tin is employed as the low melting metal, an alloy layer of $Cu_6Sn_5$ is formed by metallization but mechanical properties such as tensile strength are deteriorated when $Cu_6Sn_5$ is excessively formed. It is considered that elastic modulus of the conductive paste after cured is increased because excessive formation of $Cu_6Sn_5$ is suppressed by formation of $(Cu, Ni)_6Sn_5$ when nickel is added to a copper alloy powder, resulting in improving long-term reliability of mechanical properties.

The silver-coated copper alloy powder and other high melting metal powder can be employed together so long as it is not contrary to the object of the present invention. Examples of the high melting metal powder include metal powders comprising a single metal selected from gold (melting point: 1064° C.), silver (melting point: 961° C.), copper (melting point: 1083° C.) or nickel (melting point: 1455° C.).

The shape of the metal powder particle is not particularly limited, but conventionally used shape such as dendrite shape, spherical shape, flaky shape and so on can be employed. Furthermore, although the particle diameter is not limited either, but the average of that is preferably in a range from about 1 μm to 50 μm, and more preferably from 1 to 30 μm.

The content of the metal powder is preferably from 200 to 1900 parts by mass of the low melting metal powder (B) having a melting point of 240° C. or lower and from 400 to 2200 parts by mass of the high melting metal powder (C) containing the silver-coated copper alloy powder and having a melting point of 800° C. or higher, with respect to 100 parts by mass of the dimer acid-modified epoxy resin (A). It is more preferably from 700 to 1600 parts by mass of the low melting metal powder (B) and from 700 to 1600 parts by mass of the high melting metal powder (C), with respect to 100 parts by mass of the dimer acid-modified epoxy resin (A), from the standpoint of a viscosity of the paste and the balance between pot life and long-term reliability.

The content ratio (mass ratio, hereinafter the same) between the low melting metal powder and the high melting metal powder is in a range preferably from 8:2 to 2:8, and more preferably from 3:7 to 7:3. The proportion of the silver-coated copper alloy powder in the high melting metal powder is preferably from 30 to 100 mass %, and more preferably from 50 to 100 mass %.

The curing agent as the component (D) employed in the present invention contains a hydroxy group-containing aromatic compound, and one kind or a combination of two or more kinds selected from the group consisting of a phenol type curing agent and a naphthol type curing agent is preferably employed as the hydroxy group-containing aromatic compound. By employing those curing agents together with the components (A), (B), (C) and (E) as described above in the present invention, pot life of the conductive paste and long-term reliability after cured can be improved.

The phenol type curing agent and naphthol type curing agent are preferably a phenol type curing agent having a novolac structure and a naphthol type curing agent having a novolac structure, from the standpoint that heat resistance and moisture resistance are excellent. Examples of the phenol type curing agent commercially available include MEH-7700, MEH-7810 and MEH7851-4H (manufactured by Meiwa Plastic Industries, Ltd.), GPH (manufactured by Nippon Kayaku Co., Ltd.), TD2093-60M, TD-2090-60M, LF-7911, LF-6161, LF-4871, LA-7052, LA-7054, LA7751, LA-1356 and LA-3018-50P (manufactured by DIC Corporation). Examples of the naphthol type curing agent commercially available include NHN and CBN (manufactured by Nippon Kayaku Co., Ltd.), and SN170, SN180, SN190, SN475, SN485, SN495, SN375 and SN395 (manufactured by Tohto Kasei Co., Ltd.).

The curing agent (D) can contain a conventional curing agent other than the hydroxyl-containing aromatic compound so long as it is not contrary to the object of the present invention.

The content of the curing agent (D) is preferably from 1.0 to 20.0 parts by mass, and more preferably from 7.0 to 15.0 parts by mass, with respect to 100 parts by mass of the dimer acid-modified epoxy resin (A), from the standpoints of pot life and long-term reliability.

The flux as the component (E) promotes metallization of the metal powders described above, and a flux containing polycarboxylic acid is employed in the present invention. Examples of the polycarboxylic acid that can be used as the flux include dicarboxylic acids such as oxalic acid, glutaric acid, adipic acid, succinic acid, sebasic acid, malonic acid, maleic acid, fumaric acid, phthalic acid, pimelic acid, suberic acid, azelaic acid, terephthalic acid, citraconic acid, α-ketoglutaric acid, diglycolic acid, thiodiglycolic acid, dithiodiglycolic acid, 4-cyclohexene-1,2-dicarboxylic acid, dodecanedioic acid, diphenyl ether-4,4'-dicarboxylic acid, pyridine-2,6-dicarboxylic acid, tetrahydrocarboxylic acid, hexahydrocarboxylic acid, tetrahydrophthalic acid and hexahydrophthalic acid; tricarboxylic acids such as trimellitic acid, citric acid, isocitric acid, butane-1,2,4-tricarboxylic acid, cyclohexane-1,2,4-tricarboxylic acid, benzene-1, 2,4-tricarboxylic acid and 1,2,3-propanetricarboxylic acid; and tetracarboxylic acids such as ethylenetetracarboxylic acid, 1,2,3,4-butanetetracarboxylic acid, cyclobutane-1,2,3, 4-tetracarboxylic acid and benznene-1,2,4,5-tetracarboxylic acid.

The flux (E) can contain a compound other than the polycarboxylic acid so long as it is not contrary to the object of the present invention, and examples thereof include lactic acid, citric acid, oleic acid, stearic acid, glutamic acid, benzoic acid, glycerin and rosin.

The amount of the flux (E) employed is preferably from 5.0 to 100.0 parts by mass, more preferably from 30.0 to 80.0 parts by mass, and still more preferably from 50.0 to 60.0 parts by mass, with respect to 100 parts by mass of the dimer acid-modified epoxy resin (A), from the standpoints of the balance between the progress of metallization and long-term reliability.

The conductive paste of the present invention is obtained by combining the above-described components in given amounts and sufficiently mixing. The viscosity of the paste is not particularly limited, but is preferably in a range from 1000 dPa·s to 3000 dPa·s (measured at 10 rpm using BH type viscometer with rotor No. 7) from the standpoint of good printability.

Additives that have conventionally been employed in a conductive paste can be added to the conductive paste of the present invention so long as it is not contrary to the object of the present invention. Examples of the additives include a defoaming agent, a viscosity modifier and an adhesive.

When the conductive paste of the present invention obtained as described above is heated under certain conditions, there occurs curing of the resin along with fusion of the metal powders. Hence, when the conductive paste is used in filling a hole of a multilayer board, the adjacent metal powders are connected to each other and are integrated (this is hereinafter referred to as "metallization"), and additionally the metal powder is connected to the end surface of a conductive layer in the hole so as to be integrated. As a result, high conductivity is obtained compared with the case that metal powders merely contact with each other or the metal powder is merely brought into contact with the end surface of the conductive layer, moreover the reliability of connection at the end surface of the conductive layer is remarkably improved. Furthermore, the conductive paste has excellent adhesion to the insulating layer of the multilayer board so that a multilayer board having high long-term reliability can be obtained.

The multilayer board using the conductive paste of the present invention and its production method are described below with reference to the drawing.

Figure 1B:
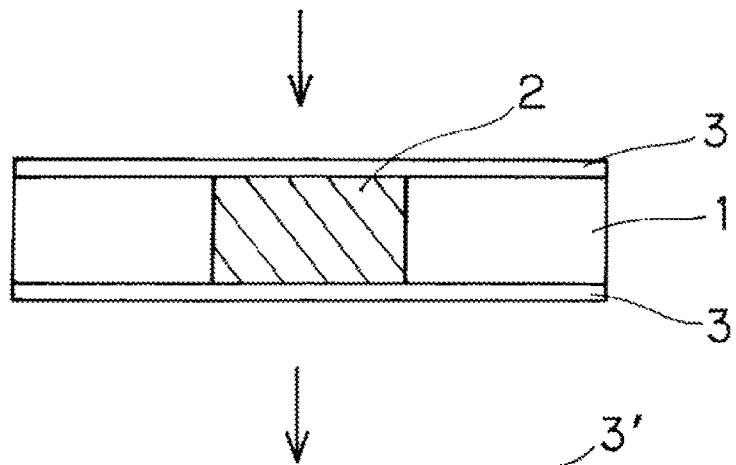
Figure 1C:
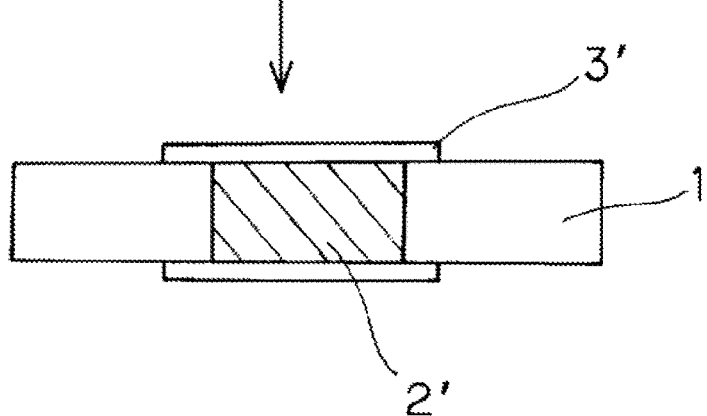

FIG. 1 is an enlarged schematically cross-sectional view showing an example of the production of a multilayer board using the conductive paste of the present invention. In FIG. 1, reference numeral 1 indicates a prepreg, reference numeral 2 indicates a conductive paste filled in a through-hole of the prepreg 1, reference numeral 3 indicates a copper foil, reference numeral 2' indicates a cured conductive paste 2, and reference numeral 3' indicates a patterned copper foil. The drawing shows an example in which through-hole plating is not applied to a through-hole of the board and a filled material is directly brought into contact with an inner wall of the through-holes.

To obtain the board shown in the drawing, for example, a through-hole is formed in a preheated prepreg 1 by a drill or laser, and the conductive paste 2 is then filled in the through-hole, as shown in (a). The copper foil 3 is provided on the upper and lower surfaces of the prepreg 1, and pressed to integrate with the prepreg as shown in (b), followed by heating under certain conditions. Since the resin component is cured and the metal powders are fused by the heating, metallization that the adjacent metal powders are integrated with each other proceeds as well as the metal powder is strongly bonded to the end surface of the copper foil. After curing, patterning, for example, can be performed if necessary, as shown in (c).

Since heating condition of the conductive paste is selected so as to be suitable for both curing of the resin component and the metallization of the metal powder, a specific heating condition varies according to the composition of each paste. As a rough indication, the conductive paste is heated at a temperature in a range around from 150 to 180° C. for from about 30 to 120 minutes or so. The drawing shows the case that the conductive layer is two layers and the insulating layer is one layer, but a multilayer board in which three or more conductive layers and two or more insulating layers are alternately laminated can be produced in the same way as the above.

EXAMPLES

Examples of the present invention are described below, but the invention is not construed as being limited to those.

Examples 1 to 11 and Comparative Examples 1 to 9

Each component was combined in the proportion (parts by mass) shown in Tables 1 and 2, and mixed to prepare a conductive paste. Viscosity, pot life, conductivity (specific resistance) and resistance value of each paste were measured and the change rates of the resistance values were obtained and evaluated. The details of each component used and evaluation methods are as follows. The results are shown in Tables 1 and 2.

Modified epoxy resin: "jER871" manufactured by Mitsubishi Chemical Corporation

Phenol type curing agent: "TAMANOL 758" manufactured by Arakawa Chemical Industries, Ltd.

Low melting metal powder: Sn—Bi alloy metal powder (Sn:Bi=42:58, melting point: 138° C., average particle diameter: 20 μm)

High melting metal powder: alloy powder of copper and zinc (Zn) and/or nickel (Ni) coated with a silver-containing layer (Contents of Zn and Ni in an alloy powder are shown in Tables 1 and 2, and the remainder is copper. Average particle diameter: 3 μm) manufactured by DOWA Electronics Flux: 8-Ethyloctadecanedioic acid manufactured by Okamura Oil Mill Co., Ltd.

<Pot Life of Conductive Paste>

Initial viscosity of each paste was measured using BH type viscometer rotor with No. 7 (10 rpm), and pot life was determined by the time frame during which the viscosity change rate to the initial viscosity is maintained within 20% at 25° C. In the case that the time frame for the change rate to be maintained within 20% exceeds 190 hours, it is considered to be acceptable.

<Specific Resistance of Cured Conductive Paste>

Specific resistance($\times 10^{-4}$ Ω·cm): A conductive paste was line-printed (length: 60 mm, width: 1 mm, thickness: about 100 μm) on a glass epoxy board by using a metal plate, and was cured by heating at 180° C. for 60 minutes. Thus, a board for evaluation having a conductive pattern formed thereon was prepared. Resistance value between both ends of the conductive pattern was measured using a tester, and specific resistance was calculated from a cross-sectional area (S, cm$^2$) and a length (L, cm) by the following formula (1). Five lines were printed on each of three glass epoxy boards, thus forming 15 conductive patterns in total, and an average value of those specific resistances was obtained.

$$\text{Specific resistance}=(S/L)\times R \tag{1}$$

<Preparation of Board for Heat Cycle Test, Heat Resistance Test and Moisture Resistance Test>

Prepreg ("R-1551" manufactured by Panasonic Corporation) having a thickness of about 100 μm was used, and a 169 hole-connected pattern each having a diameter of 100 μm was prepared in the prepreg using $CO_2$ laser. A conductive paste was filled in the hole by a printing method, and pressing was performed under the following pressure and temperature conditions by using a vacuum press machine.

Pressure: Taking 17 minutes for surface pressure to increase from 0 kg/cm$^2$ to 10.2 kg/cm$^2$ and maintaining the pressure for 10 minutes. Next, taking 24 minutes for the surface pressure to increase to 30.6 kg/cm$^2$, maintaining the pressure for 46 minutes, and then taking 23 minutes to depressurize it to 0 kg/cm$^2$.

Temperature: Taking 17 minutes for temperature to increase from 30° C. to 130° C. and maintaining at the temperature for 10 minutes. Next, taking 24 minutes for the temperature to increase to 180° C., maintaining at the temperature for 46 minutes, and then taking 23 minutes for decreased to 30° C.

<Change Rate of Resistance Value Before and After Heat Cycle (HC) Test>

As a heat cycle test, heat cycle which comprises keeping at −65° C. for 30 minutes and keeping at 125° C. for 30 minutes was performed 1000 cycles. The resistance value was obtained as follows; resistance values of both ends of the connected pattern was measured, the resistance value was divided by the number of holes to obtain resistance value per one hole, and an average value was calculated. Regarding the sample after the heat cycle test, the average of resistance value was obtained likewise.

The change rate of resistance value before and after the heat cycle test was obtained by the following formula wherein resistance value measured before the test is "a" and resistance value measured after the test is "b". The case where the resistance value change rate is within ±20% was evaluated as "A", the case where the resistance value change rate was larger than ±20% and within ±50% was evaluated as "B", and the case where the resistance value change rate was larger than ±50% was evaluated as "C". The indication "−" means that the resistance value was too large to be measured.

$$\text{Resistance value change rate}(\%)=(b-a)\times 100/a$$

<Change Rate of Resistance Value Before and After Heat Resistance Test and Moisture Resistance Test>

Change rate of resistance value before and after heat resistance test and moisture resistance test was measured in the same manner as in the heat cycle test. The heat resistance test was conducted by allowing a sample to stand at an environmental temperature of 100° C. for 1000 hours, and the moisture resistance test was conducted by allowing a sample to stand at an environmental temperature of 85° C. and humidity of 85% for 1000 hours.

TABLE 1

|  | Example 1 | Example 2 | Example 3 | Example 4 | Example 5 | Example 6 | Example 7 | Example 8 | Example 9 | Example 10 | Example 11 |
|---|---|---|---|---|---|---|---|---|---|---|---|
| (A) Dimer acid-modified epoxy resin | 100 | 100 | 100 | 100 | 100 | 100 | 100 | 100 | 100 | 100 | 100 |
| (B) Low melting metal powder | 750 | 750 | 750 | 750 | 750 | 750 | 1800 | 250 | 1550 | 750 | 750 |
| (C) High melting metal powder (CuNiZn) Ni = 1 mass %, Zn = 10 mass % | 1550 | — | — | — | — | — | — | — | — | — | — |
| (CuNiZn) Ni = 3 mass %, Zn = 10 mass % | — | 1550 | — | — | — | — | 500 | 2050 | — | — | — |
| (CuNiZn) Ni = 5 mass %, Zn = 10 mass % | — | — | 1550 | — | — | — | — | — | — | — | — |
| (CuNiZn) Ni = 10 mass %, Zn = 10 mass % | — | — | — | 1550 | — | — | — | — | — | — | — |
| (CuZn) Zn = 5 mass % | — | — | — | — | 1550 | — | — | — | — | — | — |
| (CuZn) Zn = 10 mass % | — | — | — | — | — | — | — | — | — | 1550 | — |
| (CuNi) Ni = 5 mass % | — | — | — | — | — | 1550 | — | — | 700 | — | — |
| (CuNi) Ni = 10 mass % | — | — | — | — | — | — | — | — | — | — | 1550 |
| (D) Phenol type curing agent | 12.5 | 12.5 | 12.5 | 12.5 | 12.5 | 12.5 | 12.5 | 12.5 | 12.5 | 12.5 | 12.5 |
| (E) Flux | 50 | 50 | 50 | 50 | 50 | 50 | 50 | 50 | 50 | 50 | 50 |
| Pot life (hrs.) | 216 | 216 | 216 | 240 | 192 | 192 | 216 | 216 | 216 | 192 | 206 |
| Specific resistance ($\times 10^{-4}$ $\Omega \cdot$ cm) | 0.9 | 1.0 | 1.0 | 1.6 | 0.7 | 1.0 | 1.8 | 0.9 | 1.0 | 0.7 | 1.5 |
| Change rate of resistance value after HC ($-65°$ C. $\Leftrightarrow 125°$ C.) | A | A | A | A | A | A | A | A | A | A | A |
| Change rate of resistance value after heat resistance test (100° C.) | A | A | A | A | A | A | A | A | A | A | A |
| Change rate of resistance value after moisture resistance test (85° C. $\times$ 85% RH) | A | A | A | A | A | A | A | A | A | A | A |

TABLE 2

|  | Com. Ex. 1 | Com. Ex. 2 | Com. Ex. 3 | Com. Ex. 4 | Com. Ex. 5 | Com. Ex. 6 | Com. Ex. 7 | Com. Ex. 8 | Com. Ex. 9 |
|---|---|---|---|---|---|---|---|---|---|
| (A) Dimer acid-modified epoxy resin | 100 | 100 | 100 | 100 | 100 | 100 | 100 | 100 | 100 |
| (B) Low melting metal powder | — | — | 750 | 2000 | — | 2000 | — | 2000 | — |
| (C) High melting metal powder (CuNiZn) Ni = 5 mass %, Zn = 10 mass % | — | — | 1550 | 300 | 2300 | — | — | — | — |
| (CuZn) Zn = 5 mass % | — | — | — | — | — | 300 | 2300 | — | — |
| (CuNi) Ni = 5 mass % | — | — | — | — | — | — | — | 300 | 2300 |
| Other metal powder | Cu powder 2300 | Ag-coated Cu powder 2300 | — | — | — | — | — | — | — |
| (D) Phenol type curing agent | 12.5 | 12.5 | 12.5 | 12.5 | 12.5 | 12.5 | 12.5 | 12.5 | 12.5 |
| Imidazol type curing agent | — | — | 10 | — | — | — | — | — | — |
| (E) Flux | 50 | 50 | 50 | 50 | 50 | 50 | 50 | 50 | 50 |
| Pot life (hrs.) | 24 | 72 | 120 | 216 | 216 | 168 | 168 | 192 | 192 |
| Specific resistance ($\times 10^{-4}$ $\Omega \cdot$ cm) | 1.0 | 0.9 | 2.0 | 3.2 | 1.0 | 1.5 | 1.0 | 4.0 | 2.5 |
| Change rate of resistance value after HC ($-65°$ C. $\Leftrightarrow 125°$ C.) | — | — | A | C | — | C | — | C | — |
| Change rate of resistance value after heat resistance test (100° C.) | — | B | A | A | — | B | — | A | — |
| Change rate of resistance value after moisture resistance test (85° C. $\times$ 85% RH) | — | B | A | B | — | B | — | A | — |

INDUSTRIAL APPLICABILITY

The conductive paste according to the present invention is particularly preferably used for filling a hole of the above-described multilayer board, and in addition, is preferably used for conductive adhesives, electrode formation, component packaging, electromagnetic wave shielding, formation of conductive bump, and so on.

DESCRIPTION OF REFERENCE NUMERALS AND SIGNS

1: Prepreg
2: Conductive paste
3: Copper foil
2': Cured conductive paste
3': Patterned copper foil

The invention claimed is:

1. A conductive paste comprising:
   (A) resins consisting of epoxy resins and wherein the epoxy resins consist of 100 parts by mass of dimer acid-modified epoxy resin or 100 parts by mass of dimer acid-modified epoxy resin and other epoxy resins, the conductive paste further comprising:
   (B) from 200 to 1900 parts by mass of low melting metal powder having a melting point of 240° C. or lower,
   (C) from 400 to 2200 parts by mass of high melting metal powder containing silver-coated copper alloy powder and having a melting point of 800° C. or higher,
   (D) from 1.0 to 20.0 parts by mass of curing agent containing hydroxy group-containing aromatic compound, and
   (E) from 5.0 to 100.0 parts by mass of flux containing polycarboxylic acid.

2. The conductive paste according to claim 1, wherein the silver-coated copper alloy powder contained in the component (C) is a copper alloy powder containing from 1 to 40 mass % of zinc and/or from 1 to 40 mass % of nickel, which is coated with a silver-containing layer.

3. The conductive paste according to claim 1, wherein the low melting metal powder contained in the component (B) comprises indium alone and/or one element or an alloy of at least two elements selected from the group consisting of tin, lead, bismuth, copper, silver, antimony, zinc and indium.

4. The conductive paste according to claim 1, wherein the hydroxy group-containing aromatic compound contained in the component (D) is selected from the group consisting of a phenol, a naphthol and both a phenol and a naphthol.

5. A multilayer board comprising a plurality of conductive layers and insulating layers interposed among those conductive layers, wherein holes penetrating through the insulating layers are filled with cured conductive paste, and the conductive layers contacting both surfaces of the insulating layer are electrically conducted with each other through cured conductive paste,
   wherein the cured conductive paste is a cured product of the conductive paste according to claim 1.

6. The multilayer board according to claim 5, wherein the low melting metal powder and high melting metal powder are fused to integrate with each other, and are alloyed in the cured conductive paste.

7. The conductive paste according to claim 2, wherein the low melting metal powder contained in the component (B) comprises indium alone and/or one element or an alloy of at least two elements selected from the group consisting of tin, lead, bismuth, copper, silver, antimony, zinc and indium.

8. The conductive paste according to claim 2, wherein the hydroxy group-containing aromatic compound contained in the component (D) is selected from the group consisting of a phenol, a naphthol and both a phenol and a naphthol.

9. The conductive paste according to claim 3, wherein the hydroxy group-containing aromatic compound contained in the component (D) is selected from the group consisting of a phenol, a naphthol and both a phenol and a naphthol.

10. A multilayer board comprising a plurality of conductive layers and insulating layers interposed among those conductive layers, wherein holes penetrating through the insulating layers are filled with cured conductive paste, and the conductive layers contacting both surfaces of the insulating layer are electrically conducted with each other through cured conductive paste,
    wherein the cured conductive paste is a cured product of the conductive paste according to claim 2.

11. A multilayer board comprising a plurality of conductive layers and insulating layers interposed among those conductive layers, wherein holes penetrating through the insulating layers are filled with cured conductive paste, and the conductive layers contacting both surfaces of the insulating layer are electrically conducted with each other through cured conductive paste,
    wherein the cured conductive paste is a cured product of the conductive paste according to claim 3.

12. A multilayer board comprising a plurality of conductive layers and insulating layers interposed among those conductive layers, wherein holes penetrating through the insulating layers are filled with cured conductive paste, and the conductive layers contacting both surfaces of the insulating layer are electrically conducted with each other through cured conductive paste,
    wherein the cured conductive paste is a cured product of the conductive paste according to claim 4.

13. The conductive paste according to claim 1, wherein the other epoxy resins are in a proportion of up to 50 parts by mass per the 100 parts by mass of the dimer acid-modified epoxy resin.

14. The conductive paste according to claim 1, wherein the conductive paste consists of:
    (A) the one or more resins;
    (B) the low melting metal powder,
    (C) the high melting metal powder,
    (D) the curing agent, and
    (E) the flux.

* * * * *